United States Patent [19]

Chupp et al.

[11] Patent Number: 4,593,144

[45] Date of Patent: Jun. 3, 1986

[54] PROCESS FOR PREPARING SUBSTITUTED BENZOTRICHLORIDE COMPOUNDS

[75] Inventors: John P. Chupp, Kirkwood; Thomas E. Neumann, Creve Coeur, both of Mo.

[73] Assignee: Monsanto Company, St. Louis, Mo.

[21] Appl. No.: 659,393

[22] Filed: Oct. 10, 1984

Related U.S. Application Data

[63] Continuation of Ser. No. 572,775, Jan. 23, 1984, abandoned.

[51] Int. Cl.$^4$ ................ C07C 79/10; C07C 19/08; C07C 17/00; C07C 21/18
[52] U.S. Cl. ................................. 568/936; 568/937; 570/127; 570/142; 570/185; 570/195
[58] Field of Search .............. 568/936, 937, 938, 927; 570/127, 142, 185, 195

[56] References Cited

U.S. PATENT DOCUMENTS

| | | | |
|---|---|---|---|
| 2,174,513 | 10/1939 | Holt et al. ........................... | 570/127 |
| 2,491,481 | 12/1949 | Dickey ................................ | 570/127 |
| 2,586,364 | 2/1952 | McBee et al. ....................... | 570/127 |
| 2,714,125 | 7/1955 | Gerner ................................. | 570/195 |
| 2,744,941 | 5/1956 | Hartle et al. ........................ | 570/142 |
| 2,859,283 | 11/1958 | Snow ................................... | 570/195 |
| 3,125,594 | 3/1964 | Hubel et al. ........................ | 570/185 |
| 3,465,051 | 9/1969 | Pecherer ............................. | 568/936 |
| 3,830,862 | 8/1974 | Mayers et al. .................. | 260/668 C |
| 3,993,704 | 11/1976 | Marsh et al. ....................... | 260/646 |
| 4,098,831 | 7/1978 | Marsh ................................. | 260/646 |
| 4,334,111 | 6/1982 | Davis et al. ........................ | 570/195 |
| 4,467,125 | 8/1984 | Chupp et al. ....................... | 568/936 |
| 4,470,930 | 9/1984 | Tang et al. ......................... | 570/127 |
| 4,486,355 | 12/1984 | Bentley et al. ..................... | 570/127 |

FOREIGN PATENT DOCUMENTS

| | | | |
|---|---|---|---|
| 633765 | 12/1982 | Switzerland ....................... | 568/936 |
| 1024656 | 3/1966 | United Kingdom ............... | 568/936 |
| 2071087 | 9/1981 | United Kingdom ............... | 570/127 |

OTHER PUBLICATIONS

"Carbanion Halogenations with Carbontetrahalides αHaloEsters", *Journal Org Chem*, vol. 43, No. 19, (1978), p. 3687.
"Phase Transfer Catalysis", Dehmlow et al, *Weinheim*, 2nd edition, pp. 209-211.
"Reactions of Organic Anions", Makosza et al, *Rocznika Chem*, 49, 1779 (1975).
"Chlorination with Carbon Tetrachlorides . . . ", Lauritzen et al, *ACTA Chemica Scandiaavica*, B35 (1981), 263-268.
"Reactions of Carbon Tetrachloride . . . in Catalytic Two Phase Systems", *J. Org. Chem.* vol. 44, No. 7 (1979), p. 1192.
*Chem. Abs*, vol. 89 (1978), p. 903.
*Chem Abs*, vol. 84 (1976), p. 429.
*Chem Abs*, vol. 94 (1981), p. 567.
*Chem Abs*, (1981), 95:219424m.
*Chem Abs*, (1981), 95:24427.

*Primary Examiner*—Thomas Wallen
*Attorney, Agent, or Firm*—Robert B. Martin

[57] ABSTRACT

This invention pertains to a process for preparing substituted and unsubstituted benzotrichlorides. The process generally involves reacting the starting compound with a perchloroalkane with presence of base and a phase transfer catalyst.

15 Claims, No Drawings

PROCESS FOR PREPARING SUBSTITUTED BENZOTRICHLORIDE COMPOUNDS

This is a continuation of application Ser. No. 572,775, filed Jan. 23, 1984, now abandoned.

FIELD OF THE INVENTION

The present invention relates to a process for preparing substituted benzotrichloride compounds.

BACKGROUND OF THE IVENTION

Substituted benzotrichloride compounds are known in the art. These compounds are generally produced by free radical chlorination of the corresponding substituted toluene. The free radical chlorination is generally accomplished by reacting the starting compound with chlorine gas at an elevated temperature and/or in the presence of ultraviolet light or other catalyst. Free radical chlorination results generally in non-selective chlorination of alkyl substituents. Free radical chlorination also results, in some cases, in the formation of polymer by-products.

An alternative method of forming benzotrichloride compounds is disclosed in U.S. Pat. No. 4,098,831. This method generally involves reacting a starting benzyl or benzal chloride compound with a hypochlorite in the presence of a phase transfer catalyst. The patent discloses that this method is applicable to benzyl or benzal chloride compounds having a nitro substituent which is ortho or para to the benzyl or benzal chloride radical.

It is an object of the present invention to provide a new process for making substituted and unsubstituted benzotrichloride compounds.

Other objects and advantages will become apparent from the following disclosure.

SUMMARY OF THE INVENTION

The present invention relates to a new process for preparing substituted and unsubstituted benzotrichloride compounds. The process generally involves chlorination of the corresponding benzyl or benzal halide compound with a perchloroalkane chlorinating agent in the presence of base and a phase transfer catalyst. The benzyl halide starting compounds should contain a nuclear substituent which withdraws electron density from the benzene ring thereby making the benzyl halide reactive towards the perchloroalkane chlorinating agent. The benzyl starting compounds may also contain other nuclear substituents.

The benzal halide starting compounds need not contain an electron withdrawing substituent. However, they may, if desired, contain nuclear substituents and, in general, the selection of these substituents is not critical provided they do not interfere with the reaction.

The process of the present invention provides, in part, a unique method for making unsymmetrical alkyl substituted benzotrichlorides, such as 3-methylbenzotrichloride.

A more thorough disclosure of the present invention is presented in the detailed description which follows.

DETAILED DESCRIPTION OF THE INVENTION

The present invention relates to a new process for preparing both substituted and unsubstituted benzotrichloride compounds. The process generally involves chlorination of the corresponding benzyl or benzal halide compound with a $C_{1-3}$ perchloroalkane chlorinating agent in the presence of base and a phase transfer catalyst.

The preferred chlorinating agents are carbon tetrachloride and hexachloroethane. It is anticipated that in commercial operations the tetrachloroethylene by-product from chlorination with hexachloroethane could be rechlorinated and recycled. Conveniently, a molar excess of chlorinating agent is utilized in the process of the present invention, e.g., from about 1.05 to about 10 molar equivalents (moles of chlorinating agent per mole of starting compound).

The benzyl and benzal halide starting compounds can contain chlorine, bromine, or mixtures thereof. Conveniently, benzyl and benzal chlorides are used. The benzyl and benzal halide starting compounds can contain nuclear substituents. The benzyl halide should contain a nuclear substituent which withdraws electron density from the benzene ring to make the benzylic hydrogen more acidic and stabilizes the carbanion reactant thereby promoting the chlorination of the benzyl halide starting compound.

One good measure of electron withdrawal capability of a substituent is the Hammett sigma constant of the substituent. Sigma is an approximate measure of the deactivating strength (electron withdrawing capability) of a substituent. The degree of deactivation will normally be greater at the ortho and para positions. Preferably, in order to facilitate the rate and completion of the chlorination reaction of substituted benzyl halide compounds, at least one substituent will have a Hammett sigma value that is greater than about +0.45. Preferred substituents are nitro and trifluoromethyl. Other electron withdrawing substituents which do not interfere with the process of the present invention and do not adversely interact with the solvents or reactants employed in the process can also be utilized. The benzyl halide may also contain other nuclear substituents, both activating and deactivating. However, these nuclear substituents should not substantially counteract the electron withdrawing effect of the requisite deactivating substituent on the benzyl halide nor adversely interact with the solvents or reactants employed in the process. Among the suitable nuclear substituents are alkyl, haloalkyl, alkoxy, and halogen. Other suitable nuclear substituents will be known to those skilled in the art.

The benzal halide starting compounds can, if desired, contain nuclear substituents. In general, the selection of these nuclear substituents is not critical to the process of the present invention. However, these nuclear substituents should not adversely interact with the solvents or reactants employed in the process. Further, substitution at the ortho positions can retard the formation of the benzotrichloride product by steric hindrance. Among the suitable nuclear substituents are alkyl, nitro, haloalkyl, alkoxy, and halogen. Other suitable nuclear substituents will be known to those skilled in the art.

Suitable bases for use in the process of the present invention are aqueous alkali and alkaline earth metal hydroxides. Other bases will be known to those skilled in the art. A convenient and relatively inexpensive base is sodium hydroxide. Chlorination of benzyl and benzal chloride compounds is preferably accomplished in a solution having a pH of about 14 or greater. The higher pH increases the reaction rate by making the benzylic hydrogen more acidic. At a lower pH the rate of the reaction will decrease. In order to maintain the pH at the desired level, it is convenient to use an excess of base, e.g., from about 4 to about 10 molar equivalents of sodium hydroxide (moles of sodium hydroxide per mole of starting compound). Preferably, concentrated sodium hydroxide (e.g., 50%) is utilized to minimize the amount of water in the reaction mixture. Removal of water during the reaction by azeotroping will also increase the pH of the reaction mixture and enhance the rate of the reaction. It has been found that when hexachloroethane is used as a chlorinating agent, the reaction proceeds faster and less base is necessary than when carbon tetrachloride is used as a chlorinating agent.

Useful phase transfer catalysts in the process of the present invention are those containing organic-soluble cations such as those enumerated in U.S. Pat. No. 3,992,432, including ammonium, phosphonium, and sulfonium salts. Exemplary phase transfer catalysts include quaternary ammonium salts. Preferred quaternary ammonium salts are the tetraalkyl salts which contain from 12 to 16 carbon atoms, e.g., n-propylammonium chloride and dodecyltrimethylammonium chloride. Quaternary ammonium salts containing benzyl or ether linkages are not as suitable. Other phase transfer catalysts include the acyclic and cyclic polyethers which complex with the base cation and then pair with the counter anion for transport to the organic phase. Exemplary of such catalysts would include "18-crown-6" cyclic ether in combination with potassium hydroxide as base. It would be obvious to one skilled in the art that other phase transfer catalysts may also be useful in the practice of the present invention.

Normally the reaction is run without the use of any solvents. However, in some cases, it may be desirable to use an inert solvent, e.g., when solids may be present. Suitable inert organic solvents which can be used are methylene chloride, tetrachloroethylene, hexane, heptane, and 1,2-diethoxyethane. Temperature and pressure of the reaction are not critical and conveniently, the reaction is run at atmospheric pressure and a temperature of about 25° C. to about 140° C., preferably about 85° C. Conveniently, the reaction can normally be run at reflux.

The above reactants are charged into a suitable reaction vessel conveniently equipped with means for stirring and heating. The order of addition is not critical. Conveniently, about 4 molar equivalents of carbon tetrachloride and a catalytic amount of a phase transfer catalyst, e.g., 0.01 molar equivalents, are charged into the reaction vessel with the starting compound. Then about 8 molar equivalents of sodium hydroxide are added to the vessel. Less base can be used if the water formed during the reaction is removed from the reaction mixture by azeotroping. For benzyl chlorides, it has been found that, in some cases, a small amount of t-butyl alcohol promotes the reaction. The mixture is then stirred and refluxed for a period of about 1 to 8 hours. Longer reaction times may be necessary for starting compounds having an ortho substituent. However, longer reaction times may result in hydrolysis of the starting compound. After completion of the reaction, the mixture is cooled to room temperature. The product can be isolated using standard laboratory procedures. Conveniently, water is added to the mixture and the organic layer separated by phase separation. The organic layer can be washed with a suitable acid, such as dilute sulfuric acid, to remove any residual base. The organic layer is then stripped of solvent and the product purified by suitable standard procedures, such as distillation or, in some cases, fractional crystallization.

The benzotrichloride compounds prepared by the process of the present invention can be intermediates in the manufacture of benzoyl chlorides and benzotrifluorides which are known useful compounds as dyestuff intermediates, herbicide intermediates and in producing hydroxybenzophenone ultraviolet light stabilizers.

The following examples are presented to illustrate the present invention as well as some of the various embodiments of the invention. These examples are presented as being illustrative of the novel process of the invention and are not intended to be a limitation as to the scope thereof.

EXAMPLE I

Preparation of 2-Nitro-3-Methyl Benzotrichloride 1 gm of 2-nitro-3-methyl benzyl chloride dissolved in 12 ml of carbon tetrachloride was charged into a reaction vessel with 0.25 gms of tetrabutyl ammonium chloride and 13 ml of methylene chloride. 20 ml of 50% aqueous sodium hydroxide was added to the mixture and the mixture heated for about 3½ hours at 47° C. After reaction stopped, the organic phase was separated and a fresh charge of aqueous caustic phase with catalyst was added to the organic phase. The mixture was diluted with water, solvent evaporated to give 0.80 gms of crude which was purified by distillation at 110° C. to 120° C. (0.02-0.05 mm/Hg 0.026-0.067 $\times 10^5$ pascals) to give a colorless oil which crystallized. Recrystallization from methanol gave colorless crystals. m.p. 61–62° C. Elemental analysis for $C_8H_6Cl_3NO_2$:

|  | C | H | N | Cl |
|---|---|---|---|---|
| Calculated | 37.75 | 2.38 | 5.50 | 41.79 |
| Found | 37.79 | 2.38 | 5.48 | 41.76 |

EXAMPLE II

Preparation of 3-Methyl Benzotrichloride 70.0 gms of 3-methyl benzal chloride dissolved in 286.4 gms of carbon tetrachloride was charged into a reaction vessel with 2.67 gms of Aliquat 4 (dodecyltrimethylammonium chloride in alcohol). 192 gms of 50% aqueous sodium hydroxide was added and the mixture heated to reflux for a period of about 4 hours. During this period water was continuously removed from the reaction media using a Dean Stark Trap. After completion of the reaction, the mixture was filtered, water was added to the mixture, and the organic layer was separated by phase separation. The organic layer was stripped on a rotary evaporator to give 84.9 gms of a clear yellow oil. (Yield 93.4%).

EXAMPLE III

Preparation of 4-Ethyl Benzotrichloride 22.7 gms of 4-ethyl benzal chloride dissolved in 100 gms of carbon tetrachloride was charged into a reaction vessel with 2.0 gms of Aliquot 4. 150 ml of 50% sodium hydroxide was added and the mixture heated to reflux for a period of about 1 hour. After the completion of the reaction, water was added to the mixture and the organic layer separated by phase separation. The organic solvent was stripped on a rotovac and product distilled on Krughrohr to give 23.8 gms of pale yellow liquid.

(Yield 89%). [Pot temperature 90°–100° C. (at 0.15 mm/Hg - 0.2×10⁵pascals)]. Elemental analysis for $C_9H_9Cl_3$:

|  | C | H | Cl |
|---|---|---|---|
| Calculated | 48.36 | 4.06 | 47.58 |
| Found | 48.51 | 4.10 | 47.37 |

EXAMPLE IV

Preparation of 2-Chlorobenzotrichloride 23.5 gms of 2-chlorobenzal chloride was reacted in accordance with the procedure of Example III and refluxed for 3 hours to give 25 gms of a pale yellow liquid. (Yield 91%). [Pot temperature 90°–110° C. (at 0.1 mm/Hg - 0.13–10⁵pascals)].

EXAMPLE V

Preparation of 3-Chlorobenzotrichloride 23.5 gms of 3-chlorobenzal chloride was reacted in accordance with the procedure of Example III to give 22.4 gms of a clear colorless oil (Yield 81%). [Pot temperature 90°–110° C. (at 0.1 mm/Hg - 0.13×10⁵ pascals)].

EXAMPLE VI

Preparation of 3-Trichloromethylbenzotrichloride 29.3 gms of 3-dichloromethyl benzal chloride was reacted in 220 gm of 50% sodium hydroxide in accordance with the procedure of Example III to give 35.1 gms of a clear colorless oil. (Yield 93.5%). [Pot temperature 135° C. (at 1.0 mm/Hg - 0.13–10⁵ pascals)].

EXAMPLE VII

Preparation of 2-Methylbenzotrichloride 21 gms of 2-methyl benzal chloride was reacted in accordance with the procedure of Example III to give 25% yield of product after heating at reflux for 6 hours. Yield determined by GC-Mass spectral analysis.

EXAMPLE VIII

Preparation of 2-Nitro-3-Methylbenzotrichloride 1.5 gms of 2-nitro-3-methyl benzyl bromide was mixed with 0.05 gms of tetraethyl ammonium chloride in 15 ml of methylene chloride and 10 ml of carbon tetrachloride. 20 ml of 50% sodium hydroxide was added and the mixture refluxed for about 3 hours. After completion of the reaction, the organic layer was separated, washed with water, and the product separated to give 36% yield as determined by GC-Mass spectral analysis.

EXAMPLE IX

Preparation of 3-Methylbenzotrichloride 36.2 gms of 3-methyl benzal chloride in 207 gms of solvent, tetrachloroethylene, was added into a reaction vessel with 53.9 gms of hexachloroethane, 66.3 gms of 50% sodium hydroxide, and 1.4 gms of Aliquot 4. The mixture was stirred and refluxed under partial vacuum at about 90° C. for about 1 hour. 20.3 ml of water was removed from the mixture via a Dean Stark trap during this period. The mixture was refluxed for another hour an additional 10.5 ml of water was removed. 200 ml of water was added to the cooled mixture and 15 gms of HCl gas was added until the mixture turned acidic. After standing for 2 days, the organic layer was removed and the tetrachloroethylene was distilled off under reduced pressure. The remaining residue was then distilled to give 36.7 gms of a clear oil. b.p. 80°–90° C. (0.6–1.0 mm/Hg-0.8–1.33×10⁵pascals). (Yield 85% - 97.2 assay).

EXAMPLE X

Preparation of 2-Nitro-3-Methylbenzotrichloride 9.6 gms of 2-nitro-3-methyl benzal chloride (prepared by chlorination of 2-nitro-m-tolualdehyde with thionyl chloride), 9.6 gms of 2-nitro-3-methyl benzyl chloride, 0.6 gms of n-dodecyl trimethyl ammonium chloride, 160 ml of methylene chloride, 100 ml of carbon tetrachloride, 250 ml of 50% sodium hydroxide, and 10 gms of t-butyl alcohol were charged into a reaction vessel. The mixture was refluxed for 3½ hours, cooled, solvent extracted, distilled and recrystallized to 16.0 gms of product as determined by GC-Mass spectral analysis.

Although this invention has been described with respect to specific embodiments, the details thereof are not to be construed as limitations, for it will be apparent that various embodiments, changes, and modifications may be resorted to without departing from the spirit and scope thereof, and it is understood that such equivalent embodiments are intended to be included within the scope of the invention.

We claim:

1. A process for the preparation of substituted benzotrichlorides which comprises reacting a substituted benzal chloride with a $C_{1-3}$ perchloroalkane in the presence of base and a phase transfer catalyst.

2. The process of claim 1 wherein said perchloroalkane is selected from the group consisting of carbon tetrachloride and hexachloroethane.

3. The process of claim 1 wherein the pH of the reaction solution is greater than about 14.

4. The process of claim 1 wherein said base is sodium hydroxide.

5. The process of claim 1 wherein said substituted benzal chloride is 2-nitro benzal chloride.

6. The process of claim 1 wherein said substituted benzal chloride is 2-nitro-3-methyl benzal chloride.

7. The process of claim 1 wherein said substituted benzal chloride is 3-methyl benzal chloride.

8. A process for the preparation of nuclear substituted benzotrichlorides which comprises reacting a nuclear substituted benzyl chloride with a $C_{1-3}$ perchloroalkane in the presence of base and a phase transfer catalyst, said benzyl chloride having at least one electron withdrawing nuclear substituent being sufficiently electron withdrawing to make the benzyl chloride reactive with the $C_1$—perchloroalkane.

9. The process of claim 8 wherein said electron withdrawing substituent has a Hammett sigma constant which is greater than about +0.45.

10. The process of claim 8 wherein said electron withdrawing substituent is selected from the group consisting of nitro and trifluoromethyl.

11. The process of claim 8 wherein said perchloroalkane is selected from the group consisting of carbon tetrachloride and hexachloroethane.

12. The process of claim 8 wherein the pH of the reaction solution is greater than about 14.

13. The process of claim 8 wherein said base is sodium hydroxide.

14. The process of claim 8 wherein said substituted benzyl chloride is 2-nitro benzyl chloride.

15. The process of claim 8 wherein said substituted benzyl chloride is 2-nitro-3-methyl benzyl chloride.

* * * * *